United States Patent [19]

Kraft et al.

[11] 4,455,910
[45] Jun. 26, 1984

[54] TRAVERSING MICROTOME WITH AIR BEARINGS

[75] Inventors: Winfried Kraft, Asslar-Werdorf; Gerhard Pfeifer, Solms; Artur Reichel, Wetzlar; Kurt Richter, Ehringshausen-Katzenfurt, all of Fed. Rep. of Germany

[73] Assignee: Ernst Leitz Wetzlar GmbH, Wetzlar, Fed. Rep. of Germany

[21] Appl. No.: 439,314

[22] Filed: Nov. 4, 1982

[30] Foreign Application Priority Data

Nov. 6, 1981 [DE] Fed. Rep. of Germany ....... 3144120

[51] Int. Cl.$^3$ ............................................. G01N 1/06
[52] U.S. Cl. ........................................ 83/874; 83/169; 83/409; 83/718; 83/824; 83/915.5; 308/5 R
[58] Field of Search ................. 83/874, 169, 707, 713, 83/718, 409, 412, 414, 415, 824, 915.5; 308/5 R, 3 R, 3 A, 6 R, DIG. 1

[56] References Cited

U.S. PATENT DOCUMENTS 930,686  8/1909  Patterson ................. 83/915.5 X
4,099,800  7/1978  Bell ........................... 308/3 A

FOREIGN PATENT DOCUMENTS 1435266  5/1976  United Kingdom ............... 83/915.5

Primary Examiner—James M. Meister
Attorney, Agent, or Firm—Schwartz, Jeffery, Schwaab, Mack, Blumenthal & Koch

[57] ABSTRACT

Disclosed is a traversing microtome having a base (10) and a movable carriage (13). A blade holder (12) with a blade (16) is mounted on the base (10), and an object holder (14) is mounted on the carriage (13). To carry out the cutting process, the carriage (13), together with the object holder (14) and the object (15), is moved against the stationary blade (16). Between the guide rails (18,18') of the base (10) and the carriage (13) a bearing gap (30) with a width of a few microns is created by means of air bearing elements (21,21'), and consequently only a minimal force is required to move the slide (13). Between the air bearing elements (21,21'), magnets (22,22') are arranged so that their attracting forces act against the air pressure of the air bearing elements. In this manner, the force needed to arrest the motion of the carriage (13) at any given location of the guide rails (18,18') is extremely low. The carriage (13) cannot be moved when the supply of air is interrupted. The air bearing elements are suspended in the manner of a pendulum and are adjustable in height; the latter is true for the magnets (22,22') also. In view of the air bearings, no lubrication is required for the guide rails (18,18').

11 Claims, 4 Drawing Figures

TRAVERSING MICROTOME WITH AIR BEARINGS

BACKGROUND OF THE INVENTION

The present invention relates to a traversing microtome and more especially to a traversing microtome having a blade holder adjustably mounted on a base for an adjustable blade and having a carriage which is supported displaceably on guide rails with respect to the base for carrying out the cutting movement and which carries an object holder.

Traversing microtomes of this general type are known, in which the carriage has flanges on its bottom side by which it is guided along slide rails on a support or base. Because the mode of guiding the carriage is of essential importance for the quality of cuts, the production of such bearings requires a high degree of precision. In spite of this, the force to be exerted in moving the carriage is often appreciable, resulting in nonuniform moving velocities of the carriage and thus in cuts of lesser quality. Also, the maintenance of wearing parts and the lubrication of the slide bearings require a relatively great expense. The scratching of the guide rails by dust particles contained in the lubricant must be prevented, together with soiling by a mixture of lubricants, cutting residues and embedding material.

A microtome is known from DE-OS No. 1,925,364 having a carriage which is guided on round rods by means of spherical bearings. constant maintenance is not required here as the guides are provided with permanent lubrication. The latter is made vacuum tight in a manner not described in detail and, consequently, is expensive. The force applied to move the carriage is small in this case, as rolling friction is used in place of sliding friction. However, a relatively large force is needed to brake the carriage.

SUMMARY OF THE INVENTION

It is therefore an object of the present invention to provide an improved traversing microtome.

It is a particular object of the invention to provide a traversing microtome in which a minimal force is required both for the displacement and for the arresting of the carriage in the desired location of the guide rails.

Another object of the invention resides in providing a traversing microtome in which the guide rails are free of lubricant.

Still another object of the invention is to provide a traversing microtome in which the carriage cannot be moved when the microtome is not being used.

In accomplishing the foregoing objects, there has been provided in accordance with the present invention a traversing microtome, comprising a base; a blade mounted on the base; a movable carriage adapted to hold an object to be cut by the blade upon movement of the carriage with respect to the blade; guide members along which said carriage is movable with respect to the base; means for selectively creating an air-cushioned suspension of the carriage with respect to the base, whereby substantially frictionless movement of the carriage along the guide members can be achieved; and means, including at least one magnet positioned in the vicinity of one of the guide members, for urging the carriage into a stopped position with respect to the base. Preferably, the air-cushioned suspension means comprises a plurality of air bearing elements and the urging means comprises a plurality of magnets arranged along each of the guide members.

Further objects, features and advantages of the present invention will become readily apparent to those skilled in the art from the detailed description of preferred embodiments which follows, when considered together with the attached figures of drawing.

DETAILED DESCRIPTION OF PREFERRED EMBODIMENTS

Figure 1:
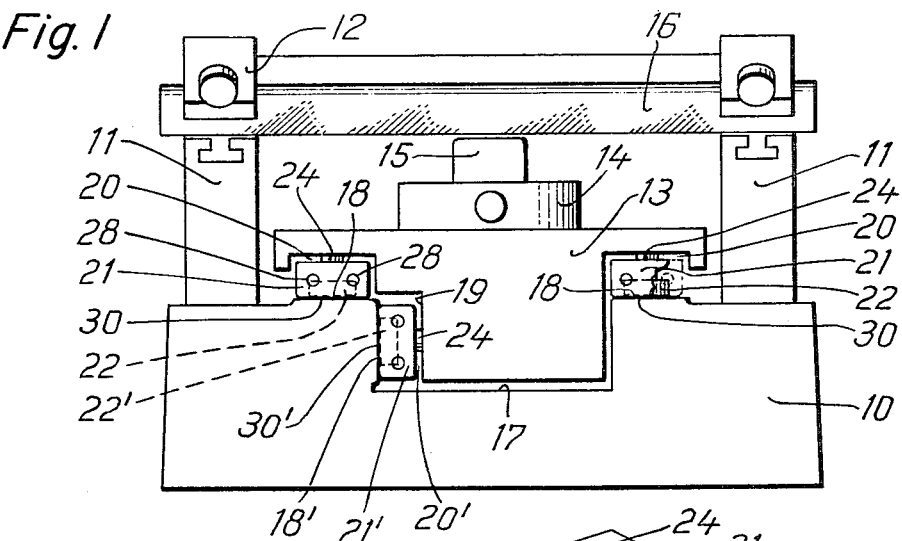
FIG. 1 is a front view of the microtome in cross-section, with all parts which are not essential to the invention being omitted.

According to the invention, bearing gaps are formed between the carriage and the base by means of air bearings and magnets are arranged along the guide rails. The use of air bearings results in extremely slight friction, whereby even during the transition from rest into the moving state no increased starting friction occurs, due to the low dynamic viscosity of air. The force required to move the carriage is practically restricted to that needed to overcome its mass inertia. On the other hand, the carriage may be arrested at any desired location merely by interrupting the advancing force, since the magnetic forces to a certain extent act as a brake, and are directed against the air flowing from the air bearing elements. If the supply of air is discontinued, the displacement of the carriage is no longer possible, since the latter is drawn onto the guide rails by a relatively high force. Lubricants are no longer required in this arrangement according to the invention, and cutting residues and dust particles are blown away by the escaping air.

A solution that is particularly simple from a manufacturing standpoint is obtained when both the air bearing elements and the magnets are arranged on the carriage, with the latter located between the air bearing elements. In many cases, for example, when electromagnets are to be used, it can be advantageous to arrange the air bearing elements, as well as the magnets between the air bearing elements, on the base, or also to arrange the air bearing elements and the magnets between them, alternatingly on the carriage and the base. It has also been found to be advantageous to mount the air bearing elements in the manner of a pendulum and adjustably on the carriage. In this manner, the air bearing elements may be always optimally adapted to the surface of the guide rails, and the placement of all of the air bearing elements in the same plane is assured. Advantageously, cylindrically shaped permanent magnets may be used as the magnets, and they are mounted in an axially displaceable manner. It is evident, however, that in the case of suitably equipped microtomes, electromagnets can also be used, as mentioned hereinabove.

In the drawing, an example of embodiment of the microtome according to the invention is shown schematically.

The microtome shown in FIG. 1 consists essentially of a box-shaped base 10 having laterally mounted platelike supports 11, upon which a displaceable blade holder 12 is bearingly supported. Also mounted on the base is carriage 13 which on its top side carriers an object holder 14, with the object 15 being clamped therein. Parallel to the cutting plane of the blade holder 12, which is displaceable in the longitudinal direction of the base 10, a blade 16 is fastened in a known manner, said blade being adjustable with respect to the cutting angle. To carry out the cutting process, the carriage 13, together with the object holder 14 and the object 15, is moved against the stationary blade 16, the following each cut the object is raised automatically by an amount corresponding to the desired thickness of cut which has been set.

Figure 2:
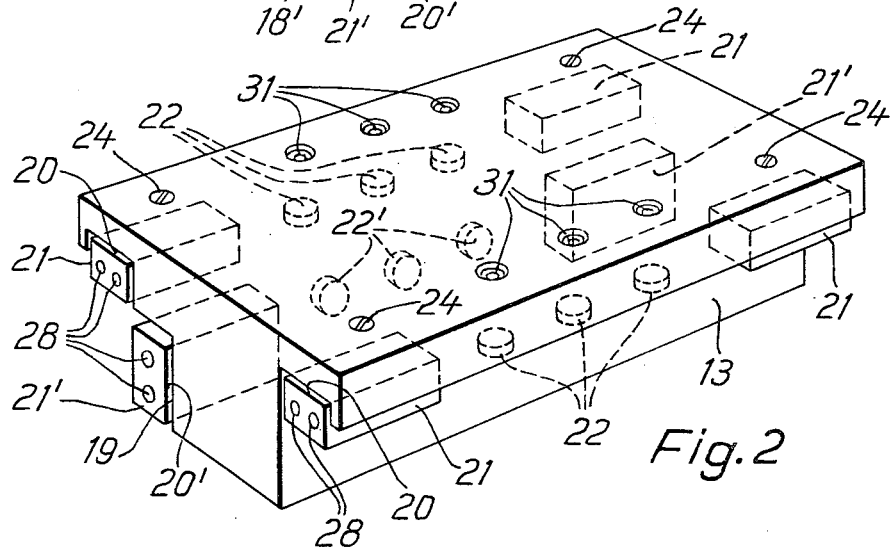
FIG. 2 is a simplified perspective view of the carriage illustrating the air bearing elements and the magnets.

The base 10 has a box-like recess 17, whereby horizontal and vertical surfaces are formed, which are equipped with finely ground steel rails to serve as guide rails 18, 18' for the carriage 13. The carriage 13 has the approximate configuration of a T-beam and is equipped on the four corners of the bottom side of its horizontal bar and at both ends of one vertical horizontal surface 19 with box-like recesses 20,20', as shown in particular in FIG. 2. The recesses 20,20' serve to receive the air bearing elements 21,21'. Between the individual air bearing elements 21,21', cylindrically shaped permanent magnets 22, 22' are provided, which hold the carriage 13 on the guide rails 18,18'.

Figure 3:
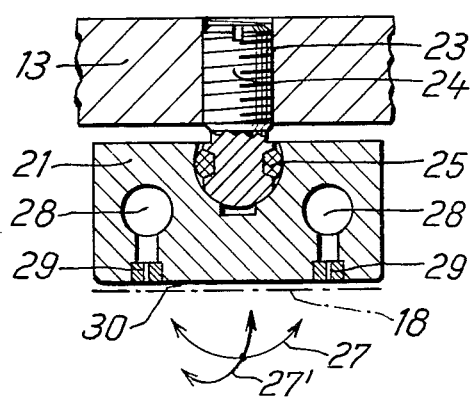
FIG. 3 is a longitudinal cross-sectional view taken through an individual air bearing element, together with its mounting.

The air bearing element 21 shown in FIG. 3 is suspended like a pendulum and is fastened displaceably. For this purpose, there is inserted in a threaded bore 23 of the carriage 13 an adjusting screw 24 which has a calotte-shaped or hemispherical configuration on its end facing the air bearing element 21 and holds the air bearing element 21 by means of a retaining ring 25 so that it is movable in the direction of the arrows 27,27'. The air bearing element 21 has a plurality of cylindrical air inlets 28, of which only two are shown here. Through these air inlets, compressed air is applied via throttle locations 29 to the guide rails 18, and a bearing gap 30 is formed between the air bearing elements 21 and the guide rails 18. In this manner, the carriage 13 is lifted off the guide rails 18 of the base 10 when air is introduced, with the weight of the slide 13 and the attracting forces of the permanent magnets 22,22' acting against the pressure of the air. In corresponding manner, a bearing gap 30' is created between the air bearing elements 21' on the longitudinal surface 19 of the carriage 13 and the vertical guide rail 18'. The width of the bearing gap is appropriately in the range of a few microns. It can be adjusted in a known manner by suitably selecting and/or dimensioning the air pressure, the inlet orifices, the attracting force of the magnets, etc. when air is supplied. The carriage 13 can be set into motion effortlessly and nearly without friction by the application of a minimal force, and it remains in motion only while said force is acting upon it, as otherwise the attraction forces of the permanent magnet 22,22' act in the manner of brakes, effecting a gentle but immediate arrest of the carriage 13 at any desired point of the guide rails 18,18'. After the air supply has been interrupted, the carriage 13 is immobilized on the guide rails 18 not only by its mass, but also by the magnetic forces. No further displacement of the slide 13 is then possible.

Figure 4:
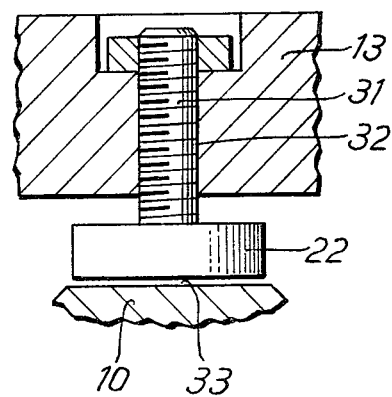
FIG. 4 is a longitudinal cross-sectional view taken through a magnet and its mounting.

The cylindrically shaped permanent magnet 22 shown in FIG. 4 is fastened to an adjusting screw 31, which is axially displaceable in a threaded bore 32 passing through the carriage 13. A spacing 33 is created between the permanent magnet 22 and the respective guide rail 18 of the base 10, the magnitude of which may be adjusted, in accordance with the desired attracting moment of the magnet, by the axial displacement of said magnet. The flat base surface of each permanent magnet 22 is positioned slightly back of the bottom surfaces of the air bearing elements 21, in order to avoid damaging the guide rails 18 when the carriage 13 is placed upon them by the interruption of the supply of air.

What is claimed is:

1. A traversing microtome, comprising:
    a base;
    a blade mounted on said base;
    a movable carriage adapted to hold an object to be cut by said blade upon movement of the carriage with respect to the blade;
    guide members along which said carriage is movable with respect to said base;
    means for selectively creating an air-cushioned suspension of said carriage with respect to said base, whereby substantially frictionless movement of said carriage along said guide members can be achieved; and
    means, including at least one magnet positioned in the vicinity of one of said guide members, for urging said carriage into a stopped position with respect to said base.

2. A traversing microtome according to claim 1, wherein said air-cushioned suspension means comprises a plurality of air bearing elements and wherein said urging means comprises a plurality of magnets arranged along each of said guide members.

3. A traversing microtome according to claim 2, wherein said air bearing elements are attached to said carriage and said magnets are arranged between the air bearing elements.

4. A traversing microtome according to claim 2, wherein said air bearing elements are arranged on said base and said magnets are arranged between the air bearing elements.

5. A traversing microtome according to claim 2, wherein said air bearing elements and said magnets are arranged alternatingly on the carriage and the base, and wherein the magnets are arranged between the air bearing elements.

6. A traversing microtome according to claim 3, wherein said air bearing elements are pendulately attached to said carriage and include means for adjusting their height with respect to the carriage.

7. A traversing microtome according to claim 2, wherein said magnets comprise cylindrically shaped permanent magnets.

8. A traversing microtome according to claim 3, including means for adjusting the height of the magnets with respect to said carriage.

9. A traversing microtome according to claim 2, wherein said base includes an upper surface and a recess having generally vertical side walls located in said upper surface, wherein said carriage comprises on its under surface a projection adapted to fit into said recess and wherein said microtome includes at least one air bearing element positioned on said projection for creating an air-cushioned suspension between said carriage and said vertical side wall.

10. A traversing microtome according to claim 9, further comprising at least one magnet associated with said projection for executing a magnetic urging force upon said vertical side wall.

11. A traversing microtome according to claim 2, wherein each of said air-cushioned suspension means comprises a member movably attached to said carriage and comprising at least one passageway for supplying compressed air to said member and at least one air nozzle attached to said passageway for impinging compressed air against said base.

* * * * *